United States Patent [19]
Lewis et al.

[11] 3,937,716
[45] Feb. 10, 1976

[54] OXAZOLIDINE DERIVATIVES

[75] Inventors: Sheldon N. Lewis, Willow Grove; Jerome F. Levy, Dresher; Napoleon L. Horton, Philadelphia, all of Pa.

[73] Assignee: Rohm and Haas Company, Philadelphia, Pa.

[22] Filed: July 9, 1973

[21] Appl. No.: 377,377

[52] U.S. Cl. 260/307 FA; 260/75 N; 260/77.5 AQ; 260/77.5 AC; 260/77.5 R; 260/248 NS; 260/469; 260/476 R; 260/486 R; 260/566 R; 260/488 F
[51] Int. Cl.$^2$................................. C07D 263/04
[58] Field of Search............................ 260/307 FA

[56] References Cited
OTHER PUBLICATIONS
Wagner et al., Synthetic Organic Chemistry, John Wiley & Sons, Inc., New York, 1953, pp. 253–254 relied on.

Primary Examiner—Richard J. Gallagher
Assistant Examiner—Anne Marie T. Tighe

[57] ABSTRACT

New products and methods for their preparation; principally, 3-(glycidyl)-1,3-oxazolidines and derivatives thereof obtained via the reaction of a 3-(glycidyl)-1,3-oxazolidine with an amine, alcohol, sulfonate, mercaptan, azide or cyanide. Also covered are oxazolidines containing a carboxy function which are obtained by treating a 3-(glycidyl)-1,3-oxazolidine with a mono-or poly-carboxylic acid. The products are useful in improving the adhesiveness of polymers and in promoting the room temperature cure of isocyanate and anhydride polymers to afford new plastic, adhesive and coating materials.

4 Claims, No Drawings

OXAZOLIDINE DERIVATIVES

This invention relates to a new class of 3-(glycidyl)-1,3-oxazolidines and to methods for their preparation. The products are useful as intermediates and as polymer-additives which improve the adhesive properties of the polymers with which they are combined. In addition, certain of the products have utility in promoting the room-temperature cure of isocyanate prepolymers and anhydride-containing polymers to afford new plastic, adhesive and coating materials.

The 3-(glycidyl)-1,3-oxazolidines of this invention have the following general formula:

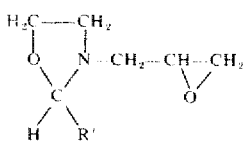
(I)

the heterocyclic portion of which is represented in simplified style or fashion in the following formulas, such as in:

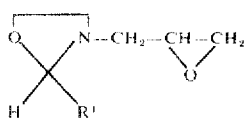
I wherein $R^1$ represents hydrogen or an hydrocarbyl radical selected from alkyl, for example, lower alkyl such as methyl, ethyl, n-propyl, isopropyl, butyl and the like, or aralkyl, for example, mononuclear and binuclear aralkyl such as benzyl, phenethyl or menaphthyl and the like. $R^1$ is an hydrocarbyl radical. The products are valuable intermediates which combine readily with polycarboxylic acids, or polymeric acids, to afford novel polyoxazolidines which have utility as polymer-additives, or as film-forming polymers, for improving the adhesiveness of said polymers to wood and painted surfaces.

Those 3-(glycidyl)-1,3-oxazolidines corresponding to formula I (supra) wherein $R^1$ is hydrocarbyl such as alkyl, are conveniently obtained by treating the corresponding 2-hydrocarbyl substituted-1,3-oxazolidine (II) with an epihalohydrin to afford a 3-(3-halo-2-hydroxypropyl)-1,3-oxazolidine (III) which, upon treatment with a base, affords the desired product (Ia). Any base which will eliminate hydrogen halide may be employed; however, we have found that the alkaline earth metal alkoxides, such as sodium methoxide in methanol, are particularly suitable for effecting dehydrohalogenation:

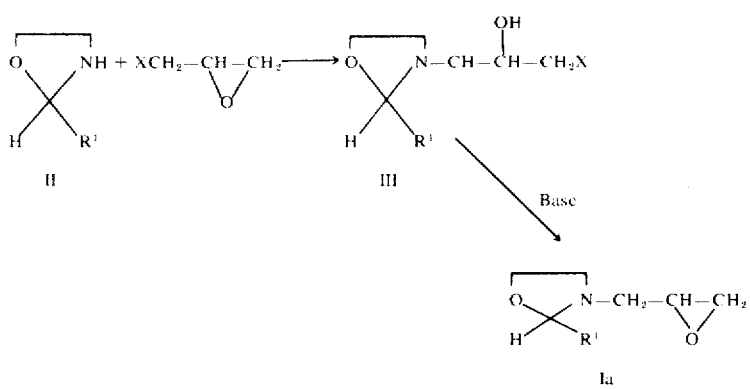

wherein X is halo as, for example, chloro, bromo or iodo and the like and $R^1$ is as defined above. Time and temperature are not especially critical to the process but, in general, it is most desirable to add the epihalohydrin to the oxazolidine over a period of several hours while maintaining the temperature at a range of from about 25°–90°C. The dehydrohalogenation step is usually conducted at temperatures of up to about 125°C. but, in general, it is preferable to operate within the range of from about −15° to about 75°C.

The above process for preparing 3-(glycidyl)-1,3-oxazolidines (I) proceeds most advantageously when the oxazolidine reactant (II) is derived from ethanolamine and an aldehyde of at least two carbon atoms. The following equation illustrates this method:

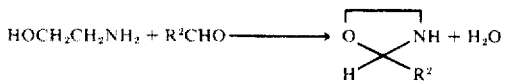
II wherein $R^2$ is alkyl, for example, lower alkyl such as methyl, ethyl, n-propyl or isopropyl and the like, or aralkyl, for example, mononuclear and binuclear aralkyl such as benzyl, phenethyl or menaphthyl and the like. To achieve maximum yield it is advisable to use stoichiometric amounts of the ethanolamine and aldehyde reactants. If an excess of aldehyde is employed the process may result in the formation of an enamine:

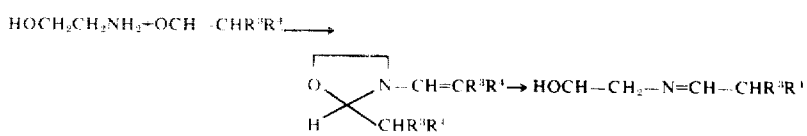

wherein $R^3$ and $R^1$ are the same or different and represent hydrogen, lower alkyl, for example, methyl, ethyl, n-propyl or isopropyl and the like or aryl for example, mononuclear and binuclear aryl such as phenyl or naphthyl and the like. Also the following products were observed upon treating ethanolamine with isobutyraldehyde:

wherein $x$ is an integer having a value of more than one. Monomeric 1,3-oxazolidine has reportedly been prepared from the reaction of formaldehyde and ethanolamine by P. A. Laurent, Compte Rendue Acad. Science, Paris, Vol. 261: pages 1323–1326 (1965).

A 3-(glycidyl)-2,2-dihydro-1,3-oxazolidine derivative (Ib) can be obtained by subjecting the 3-(3-halo-2-

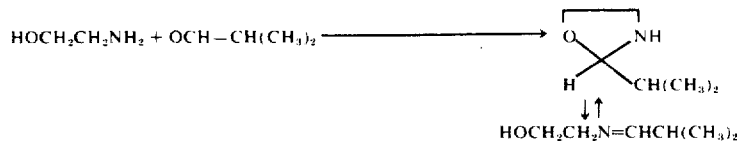

In general, the process does not afford good yields when the oxazolidine (II) is derived from formaldehyde; however, in an attempt to synthesize 3-(glycidyl)-2,2-dihydro-1,3-oxazolidine via the reaction of formaldehyde with ethanolamine and then reacting the product with an epihalohydrin, and finally dehydrohalogenating with a base, there would be obtained a small amount of product (Ib). The low yield is attributed to the competitive polymerization of the 2,2-dihydro-1,3-oxazolidine intermediate (IV) which, presumably, is catalyzed by traces of moisture and other proton sources:

hydroxypropyl)-2-hydrocarbyloxazolidine intermediate (III) to aldehyde interchange. Thus, for example, upon treating a 3-(3-halo-2-hydroxypropyl)-2-hydrocarbyloxazolidine (III) with a 37% formalin solution there is obtained a 3-(3-halo-2-hydroxypropyl)-2,2-dihydro-1,3-oxazolidine (V) and an aldehyde side product which may be removed continuously as formed. The reaction is conducted at a temperature of from about −15° to 75°C. and, preferably, at a range of from about 5°–10°C. The 3-(3-halo-2-hydroxypropyl)-1,3-oxazolidine (V) is then treated with an alcoholic

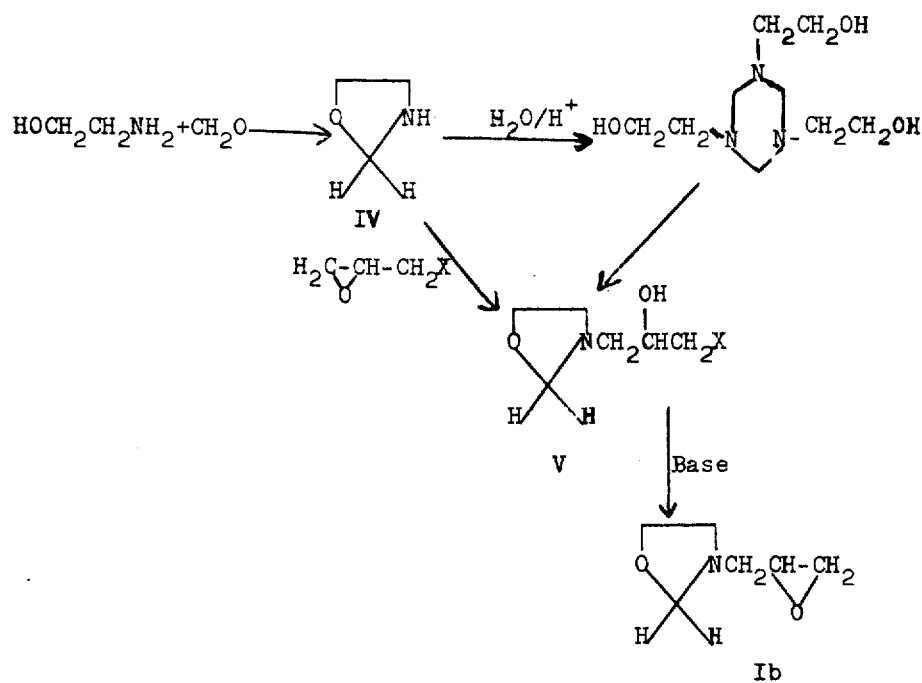

wherein X is as defined above. Also, when formaldehyde is treated with ethanolamine there is obtained, in addition to the desired monomeric oxazolidine, a cyclic trimer and various linear polymers:

solution of an alkali metal alkoxide such as sodium methoxide in methanol, to afford the desired 3-glycidyl-2,2-dihydro-1,3-oxazolidine:

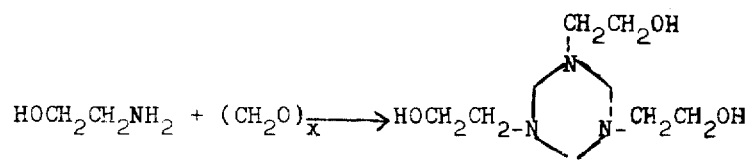

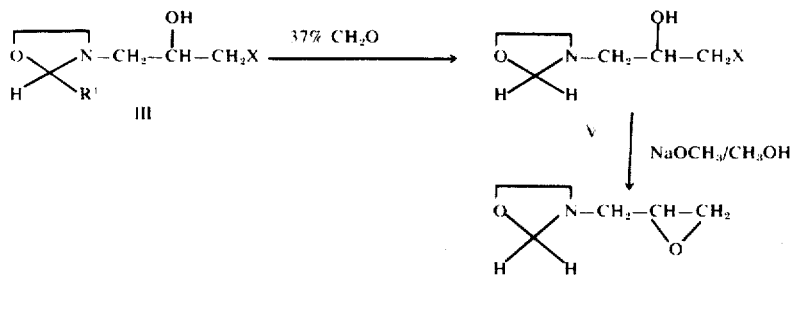

wherein R¹ and X are as defined above.

The 3-(glycidyl)-1,3-oxazolidines (I) of this invention have utility as intermediates inasmuch as they combine with a variety of nucleophilic reagents via the oxirane (i.e., epoxide) function to afford new monomeric and polymeric substances. Thus, for example, the oxirane moiety will react with the following classes of compounds to afford oxazolidine-functionalized products having a wide variety of industrial applications: primary and secondary amines, alkoxides, sulfonates, mercaptans, azides, cyanides and alcohols. The following equation illustrates this method of preparation:

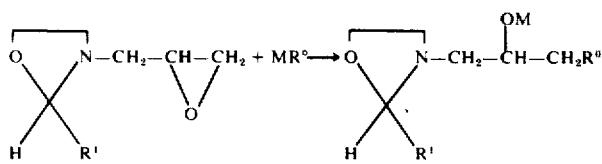

wherein MR⁰ is an amine of the formula HNR⁷R⁸, (M being H and R⁰ being —NR⁷R⁸ in that case), a primary alcohol HOR¹²(M being H and R⁰ being —OR¹² in that case), an alkoxide, an alkali metal thiosulfate (M being an alkali metal and R⁰ being S₂O₃), a mercaptan of the formula HSR³ (M being H and R⁰ being —SR³ in that case), an alkali metal azide or an alkali metal cyanide each of which are defined further in the following paragraphs; and R and R¹ are as defined above.

Polymers containing the above oxazolidines display improved adhesion to wood and painted surfaces. In addition, the 3-(glycidyl)-1,3-oxazolidines (I) provide an excellent means for incorporating the said oxazolidine moiety into carboxylic acid-containing polymers and polyesters via post-reaction of said polymers and polyesters with the oxirane moiety of the 3-(glycidyl)-1,3-oxazolidine (I). This approach, applied to acid-terminated polyesters is especially attractive for the preparation of polyoxazolidines sufficiently low in molecular weight (500–2,500) so as to be of interest in low solvent, high concentration formulations. Reactive blends of polyoxazolidines with polyisocyanates and polyanhydrides are of considerable interest in a variety of applications including industrial coatings, leather finishings and adhesives. Mixtures of diisocyanates with the 3-(glycidyl)-1,3-oxazolidines of this invention at ambient conditions (≈23°C., 40% relative humidity) produce films which rapidly become tack-free. For example, upon combining the 3-(glycidyl)-1,3-oxazolidine and diisocyanate at 23°C. and 40% relative humidity there is obtained within 2–3 hours a tack-free, hard, clear and abrasion-resistant film. In several screening tests, diisocyanate-oxazolidine mixtures provided significant improvements in leather properties when used as solvent impregnants. Improvements in early and cured peel strength and fabric bonding application was also observed.

The reaction of the instant oxazolidines (I) with secondary amines is very slow in the absence of a catalyst but it responds well to the addition of a small amount of a strong acid such as a 5% solution of para-toluenesulphonic acid:

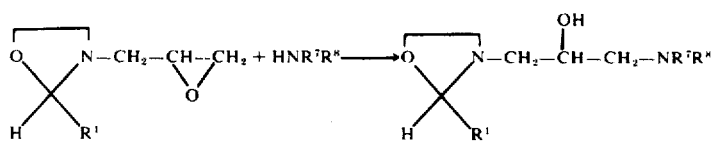

wherein R⁷ and R⁸ represent the same or different radicals selected from hydrogen, alkyl, for example, lower alkyl such as methyl, ethyl, propyl, butyl and the like; aryl, for example, mononuclear aryl such as phenyl or p-tolyl and the like; aralkyl, for example, mononuclear aralkyl such as benzyl, phenethyl and the like or, taken together with the nitrogen atom to which they are attached, the R⁷ and R⁸ radicals may be combined to form a heterocycle selected from pyrrolidino, piperidino, morpholino or oxazolidino and the like; and R and R¹ are as defined above. Temperature is not critical to the process and, in general, this reaction proceeds favorably at temperatures in the range of from about 0°C. to about 125°C. Also, the reaction proceeds readily with all classes of amines including dialkylamines but, in general the reaction with less sterically hindered amines, such as morpholine, pyrrolidine, piperidine, or oxazolidine, is distinctly more reactive. Thus 85% of pyrrolidine was consumed after 17 hours reaction with 3-(glycidyl)-1,3-oxazolidine at room temperature, whereas, with a weaker base such as morpholine, after a 20-hour reaction at 60°C. there was an approximately 90% consumption of the reactant.

In general, primary alcohols are unreactive with 3-(glycidyl)-1,3-oxazolidines under neutral or acidic conditions, but, the presence of an alkoxide, such as sodium methoxide, promotes the addition. Thus, the addition of a 3-(glycidyl)-1,3-oxazolidine (I) with excess alcohol in the presence of an alkoxide affords a 3-(3-alkoxy-2-hydroxypropyl)-1,3-oxazolidine according to the following equation:

process, the corresponding (3-thiosulfato-2-hydroxypropyl)oxazolidine salt is obtained:

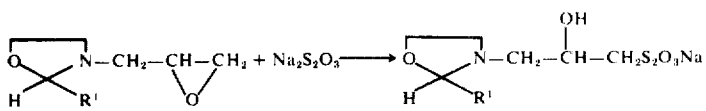

wherein $R^1$ is as defined above. Also, upon substituting an alkali metal azide or alkali metal cyanide such as sodium azide or sodium cyanide for the sodium thiosulfate described in the preceding equation, there is obtained the corresponding azido or cyano substituted oxazolidine according to the following two equations:

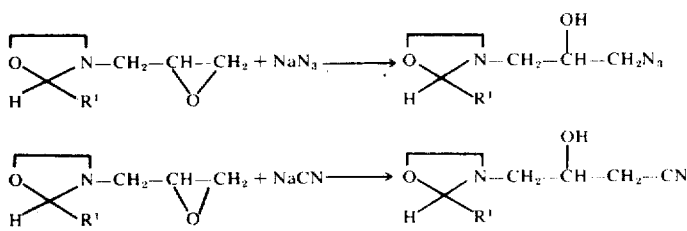

wherein $R^1$ is as defined above.

The instant 3-(glycidyl)-1,3-oxazolidines (I) also react with monocarboxylic acids, as well as with polymeric and bis-carboxylic acids in non-aqueous systems

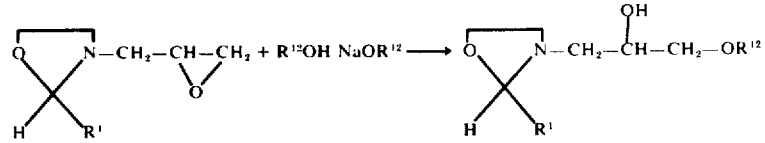

wherein R and $R^1$ are as defined above and $R^{12}$ is lower alkyl such as methyl, ethyl, propyl, butyl or amyl and the like.

The 3-(glycidyl)-1,3-oxazolidines (I) of this invention also combine with mercaptans, alkali metal thiosulfates, azides and cyanogens to afford the corresponding 3-(3-substituted -2-hydroxypropyl)-1,3-oxazolidine. Thus, for example, 3-(glycidyl)-1,3-oxazolidine (I) reacts with mercaptans according to the following equation:

to afford oxazolidine-containing esters or polyoxazolidines (VIII). The relative stability of those 3-(glycidyl)-1,3-oxazolidines (I) wherein $R^1$ is an hydrocarbyl radical makes it possible to condense same with carboxylic acids at elevated temperatures of from about 80° to about 85°C. over a period of several hours. In general, the proportion of 3-(glycidyl)-1,3-oxazolidine (I) to carboxylic acid is not critical to the process. Stoichiometric mixtures consistently resulted in yields of 65–70% conversion to ester product but an excess of

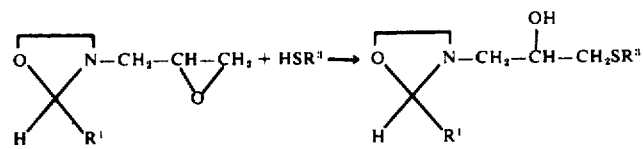

wherein $R^1$ and $R^3$ are as defined above. If, in the foregoing equation an alkali metal thiosulfate is substituted for the mercaptan ($HSR^3$) in an otherwise analogous 3-(glycidyl)-1,3-oxazolidine (I) generally resulted in an increase in the yield of product. The following equation illustrates this process:

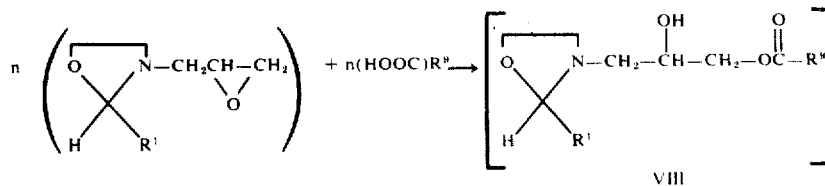

wherein $R^9$ is a covalent bond (as in oxalic acid), an alkylene chain of 2–10 carbon atoms, an alkenylene chain of 2–10 carbon atoms, arylene, for example, a mononuclear arylene, such as phenylene, or an alkenyl group of 2–10 carbon atoms, n is an integer having a value of 1 or 2. $(HOOC)R^9$ is a mono or polycarboxylic acid containing from 2–10 carbon atoms and R and $R^1$ are as defined above. Illustrative of the carboxylic acids which can be employed are, for example, oxalic acid, maleic acid, adipic acid, azelaic acid, acrylic acid. The reaction is effected by simply mixing the reactants, either directly or in an inert solvent, and applying heat. The use of a catalyst in the process is purely optional but tetraalkylammonium salts or tertiary amines are preferred. When stoichiometric amounts of the reactants are employed there is a conversion of approximately 65–70% of the available acid functionality to oxazolidine. A side reaction such as polymerization, oligomerization or rearrangement of the glycidyloxazolidine takes place in competition with the desired addition to the carboxy group and this accounts for the moderate degree of conversion. Higher conversions of up to 90% can be achieved by employing excess glycidyloxazolidine.

The polyoxazolidines (VIII) obtained via the foregoing process have many industrial uses but, as a practical matter, their actual application may be hindered by interference from residual unconverted carboxylic acid. However, this drawback may be eliminated by the post-reaction of said acid with another epoxide such as ethylene oxide.

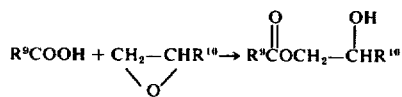

wherein $R^9$ is as defined above and $R^{10}$ is hydrogen or methyl. In this manner any residual acid is effectively eliminated via conversion to a product (IX) which is compatible with the ester-containing oxazolidine product.

The polyoxazolidines (VIII) are particularly valuable in promoting the room temperature cure of isocyanate and anhydride pre-polymers to afford plastics, coatings and adhesives with outstanding mechanical properties. The exposure of a freshly prepared mixture of an aliphatic diisocyanate 4,4'-methylene-bis(cyclohexylisocyanate) with a polyoxazolidine (VIII) at 25°C resulted in a system which had a short gel time but, the exposure of freshly-mixed systems to ambient conditions ($\approx$23°C., 40% relative humidity) produced films which were tack free within 2–3 hours and which were hard, clear and abrasion resistant within 24 hours. In several initial screening tests diisocyanate polyoxazolidine mixtures provided significant improvements in leather properties when used as solvent impregnants. In addition, an improvement in early and cured peel strength in fabric bonding application was also observed.

The reaction between the polyoxazolidines (VIII) and polyisocyanates is initiated by the presence of moisture. Atmospheric moisture is generally sufficient to initiate the polymerization and effect a cure of the composition. Also, if desired, water may be added to the compositions to effect the cure. It is believed that the polymeric products are the result of a rapid hydrolysis of the polyoxazolidines (VIII) whereupon the oxazolidine ring is opened and an amino alcohol is formed. The said amino alcohol then reacts with the polyisocyanates at either the active hydrogen of the amino group or the active hydrogen of the hydroxy group but it is believed that the reaction preferably occurs at the amino nitrogen. This process, namely, hydrolysis of the polyoxazolidine ring and subsequent polymerization with a polyisocyanate, generally occurs quite rapidly at ambient temperatures but elevated temperatures may be used if desired. The following equation wherein the polyisocyanate is a diisocyanate i.e., $R^{11}$ $+NCO)_2$, illustrates this method of preparation; however, it is to be understood that other polyisocyanates can be substituted therefor in an otherwise analogous process to afford the corresponding product:

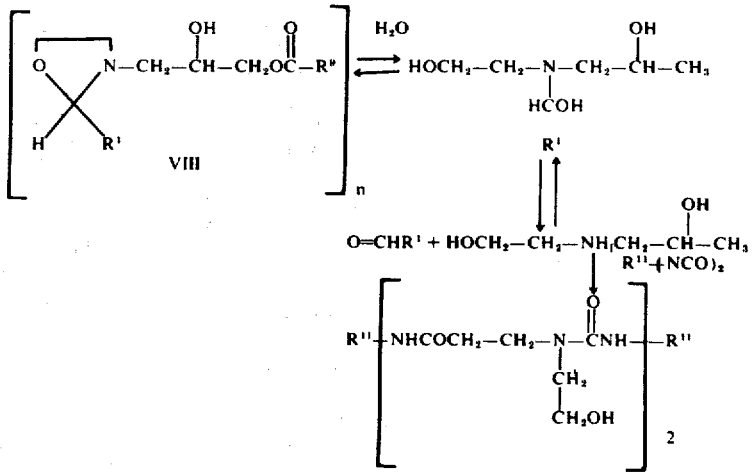

wherein the polyoxazolidine (VIII) is as defined above and $R^{11}$ $+NCO)_2$ is a diisocyanate.

The ratio of polyisocyanate to polyoxazolidine (VIII) is not critical and can vary over a wide range to influence the nature and property of the desired polymeric product. For example, the polyisocyanate and polyoxazolidine can be present in ratios such that the reaction during cure will take place primarily between the polyisocyanate and the amino group of the hydrolyzed polyoxazolidine. In general, the ratio of polyisocyanate to polyoxazolidine (VIII) is from about 1:10 to 100:1 molecular equivalents with the preferred ratio being from about 1:1.1 to about 2.5:1. Also, the reaction can be carried out with or without the use of a catalyst.

Suitable catalysts include, for example, acids such as p-toluene sulfonic acid, dibutyltin octoate, zinc chloride, hydrogen chloride or the like. The catalysts are generally employed in an amount of from about 0.001% to about 10% by weight based on the weight of polyoxazolidine and, preferably, from about 0.1% to about 5% by weight. The curing may be conducted with or without the use of a solvent but, since the rate of hydrolysis of the polyoxazolidine and the subsequent curing with polyisocyanate can be influenced by the presence of such media, solvents are generally employed. Especially preferred solvents are those which are substantially free from active hydrogen as determined by the Zerewitinoff method described in Kohler et al (Journal of the American Chemical Society, Volume 40: pages 2181–2188; 1927) and should be substantially anhydrous. Typical of these solvents are, for example, toluene, xylene, aliphatic hydrocarbons, isopropyl ether, ethyl acetate, beta-ethoxyethyl acetate, methyl ethyl ketone and the like and mixture thereof. Pigments, dyes, fillers, antiozodants, antioxidants, stabilizers, flow-control agents or other optional ingredients can also be included in the composition.

Typical of the diisocyanates which may be combined with the oxazolidines (I) of this invention are the following: saturated aliphatic and cycloaliphatic diisocyanates, unsaturated aliphatic and cycloaliphatic diisocyanates, aromatic and polyaromatic diisocyanates, isocyanates derived from aliphatic polyamines, carbonate-containing diisocyanates, di-alkyl ether containing diisocyanates, vinyl polymers containing isocyanatoethyl methacrylate as a monomer or comonomer and prepolymers of polyisocyanates with polyhydroxy or polyamino substituted alkanes and cycloalkanes. Examples of the foregoing diisocyanates include: 1,6-hexamethylene diisocyanate, 1,8-octamethylene diisocyanate, 1,12-dodecamethylene diisocyanate, 2,2,4-trimethylhexamethylene diisocyanate, 3,3'-diisocyanatodipropyl ether, 3-isocyanatomethyl-3,5,5-trimethylcyclohexylisocyanate, cyclopentylene-1,3-diisocyanate, cyclohexylene-1,4-diisocyanate, methyl 2,6-diisocyanatocaproate, bis-(2-isocyanotoethyl)fumarate, 4-methyl-1,3-diisocyanatocyclohexane, trans-vinylene diisocyanate, 4,4'-methylene-bis(isocyanatocyclohexane)methane diisocyanate N,N', N''-tris-(6-isocyanatohexamethylene) biuret, bis-(2-isocyanatoethyl) carbonate, tolylene diisocyanates, xylylene diisocyanates, dianisidine diisocyanate, 4,4'-diphenylmethane diisocyanate, 1-ethoxy-2,4-diisocyanatobenzene, 1-chloro-2,4-diisocyanotobenzene, tris-(4-isocyanatophenyl) methane, naphthalene diisocyanates, fluorene diisocyanates, 4,4'-biphenyl diisocyanate, phenylene diisocyanates, 3,3'-dimethyl-4,4'-biphenyl diisocyanate, p-isocyanatobenzyl isocyanate, tetrachloro-1,3-phenylene diisocyanate 2,4,6-tribromo-1,3-phenylene diisocyanate, bis-(2-isocyanatoethyl) benzene, 3-isocyanatomethyl-3,3,5-trimethylcyclohexylisocyanate, tolylene diisocyanate, menthane diisocyanate, menthane diisocyanate, 4,4'-methylene-bis-(cyclohexylisocyanate), 4,4'-methylene-bis-(isocyanatocyclohexane) and 2-isocyanotoethyl-6-isocyanatocaproate.

The isocyanate prepolymers of the preceding paragraph are prepared by methods well known to those skilled in the art. Generally, the preparation of the prepolymers involves the reaction of a polyol, polyether, hydroxyl-terminated polyester polyester amide, or other polyfunctional active hydrogen compound with a diisocyanate or other polyisocyanate, preferably, using an excess of the isocyanate to yield an isocyanate-terminated prepolymer product. An extensive description of some of the useful techniques for preparing the isocyanate prepolymers can be found in the text entitled: J. H. Saunders and K. C. Frisch, Polyurethanes: Chemistry and Technology, Part II, Interscience, (New York); pages 8–49 (1964).

Other polyfunctional isocyanates which can be combined with the oxazolidines (I) of this invention are those disclosed in U.S. Pat. No. 3,162,664, of Brotherton et al., granted Dec. 22, 1964; U.S. Pat. No. 3,427,346, of Brotherton et al., granted Feb. 11, 1969; U.S. Pat. No. 3,275,679, of Brotherton et al., granted Sept. 27, 1966; U.S. Pat. No. 3,352,830 1967, U.S. Pat. No. 2,729,666 of Stallmann, granted Jan. 3, 1956; U.S. Pat. No. 2,768,154 of Unruh et al., granted Oct. 23, 1956; U.S. Pat. No. 3,267,122 of Lehmann et al., granted Aug. 16, 1966; U.S. Pat. No. 3,281,378, of Garber et al., granted Oct. 25, 1966; U.S. Pat. No. 3,124,605, of Wagner, granted Mar. 10, 1964; U.S. Pat. No. 2,718,516 of Bortnick, granted Sept. 20, 1955; as well as isocyanates prepared from the amines disclosed in U.S. Pat. No. 3,256,318, of Brotherton et al., granted June 14, 1966.

The polymeric products obtained via the condensation of polyoxazolidines (VIII) with polyisocyanates have utility in forming films, fibers, paints, lacquers, varnishes, seamless caulks, coatings and impregnants and as adhesives for both natural and synthetic materials such as paper, textiles, wood, plastics, metal and leather and as binders for non-woven fabrics. To prepare coatings and films, the polymeric product can be applied with or without a solvent by casting permanently or removably onto a suitable substrate.

The Examples which follow illustrate the products of this invention and the methods by which they are obtained. However, the examples are illustrative only and it will be apparent to those having ordinary skill in the art that this invention includes functionally equivalent products and methods for their preparation. Therefore, any modification of the claimed syntheses which result in the formation of an identical product should be construed as constituting an analogous method. The claimed processes are capable of wide variation and modification and, therefore, any minor departure therefrom or extension thereof is considered as being within the skill of the artisan and within the scope of this invention.

EXAMPLE 1

3-(Glycidyl)-2-Isopropyl-1,3-Oxazolidine

Step A: 2-Isopropyl-1,3-Oxazolidine

Into a two liter, three-necked flask equipped with a bottom stopcock, mechanical stirrer, thermometer and dropping funnel was charged 305 g. (5.0 moles) ethanolamine, 35 g. (0.25 moles) anhydrous potassium carbonate and 450 cc. of toluene. To the stirred mixture was added 360 g. (5 moles) of isobutyraldehyde via a dropping funnel over a 20 minute period while the temperature rose to a maximum of 67°C. The dropping funnel was replaced with a Dean-Stark trap and the solution was stirred and allowed to cool to room temperature. The stirrer was stopped and separation of the organic and aqueous phases allowed to occur over an approximately 15 minute period. The bottom aqueous layer was removed via the bottom stopcock and the remaining solution was heated to reflux at reduced pressure (180 mm. Hg.) and the water-toluene azeotrope was collected (50 ml. water). The solution was stripped by gradually reducing the pressure to 20 mm. Hg., and continued until distillation ceased at the solution temperature of 55°C. The resulting 2 -isopropyloxazolidine (552 g., 96%) was a clear, colorless, mobile liquid.

Analysis for $C_6H_{13}NO$: Calculated: C, 62.49; H, 11.39; N, 12.15. Found: C, 61.09; H, 11.17; N, 11.35.

Neutralization Equivalent ($HClO_4$) Found: 112.9; Theoret.: 115.17.

GLC Analysis 98 + % purity.

Step B: 3-(3-Chloro-2-hydroxypropyl)-2-Isopropyl-1,3-Oxazolidine

Into a two-liter, three-necked flask equipped with a mechanical stirrer, thermometer and a dropping funnel was charged 575 g. (5.0 moles) of crude 2-isopropyl-1,3-oxazolidine. To the dropping funnel was charged 575 g. (6.25 moles) of epichlorohydrin and this material was added dropwise over a period of three hours while the temperature was maintained at 55°C ± 2°C. thru the use of controlled air cooling. After the mixture was heated at this temperature for 20 hours it was stripped of unreacted 2-isopropyloxazolidine and excess epichlorohydrin at 65°–70°C./20 mm. The crude pale yellow product thus obtained weighed 942 g. (91%) and was wiping-film distilled at 120°C./0.5 mm. to afford 705 g. (75%) of clear colorless mobile liquid identified as 3-(3-chloro-2-hydroxypropyl)-2-isopropyl-1,3-oxazolidine.

Analysis for $C_9H_{18}NOCl$: Calculated: C,52.10; H,8.72; N,6.74; Cl, 17.05. Found: C,52.36; H,8.60; N,6.56 Cl, 16.75.

E. W. ($HClO_4$) Theoret.: 207.7; Found: 205.2 GLC>96% purity.

Step C: 3-(Glycidyl)-2-Isopropyl-1,3-Oxazolidine 3-(3-Chloro-2-hydroxypropyl)-2-isopropyl-1,3-oxazolidine (621 g., 3.0 mole) was charged into a two-liter, three-necked flask equipped with a mechanical stirrer, thermometer and a dropping funnel. The flask was cooled to 0°–5°C. and 628 g. (2.91 moles) of sodium methoxide (25% solution in methanol) was added dropwise over a period of three and one-half hours. The clear solution became cloudy after several drops of base had been added. Stirring was continued for an additional two hours after addition was completed. The solution was allowed to warm to room temperature and the sodium chloride was filtered. The filtrate was concentrated on an evaporating rotary at 40°C/20 mm. and the residue was refiltered to remove the remaining sodium chloride. The solution was then stripped at 40°C/20 mm. until solvent was no longer removed. The resulting pale yellow liquid weighed 520 g. (98%) and was wiping film distilled at 100°C/0.5 mm. to afford 368 g. (71%) of 3-(glycidyl)-2-isopropyl-1,3-oxazolidine in the form of a colorless mobile liquid.

Analysis for $C_9H_{17}NO_2$: Calculated: C, 63.12; H, 10.00; N, 8.18. Found: C, 63.29; H, 9.68; N, 7.91.

Neutralization Equivalent ($HClO_4$) Calculated: 171.2; Found: 174.6.

GLC Analysis 97 + % purity with main impurity.

EXAMPLE 2

N-Glycidyl-2-Isopropyloxazolidine Esters

Into a three-necked flask (500 ml.) equipped with a mechanical stirrer, thermometer attached to a thermowatch and a condenser, was charged a polymeric acid mixture comprising methyl methacrylate, butyl acrylate and methacrylic acid (MMA/BA/MAA) in solution and 1.0 equivalent of 3-glycidyl-2-isopropyl-1,3-oxazolidine. The mixture was heated at 85°C. for 5–6 hours whereafter titrimetric data at this time indicated 60–65% of ester conversion. A 50% excess of epoxide was then added and the reaction mixture was heated an additional 4–7 hours. The resulting pale yellow solution contained 0.52 meq./g. of amine of 0.625 meq./g. of acid and a mixture of oxazolidine esters (80–85% yield) identified as: 3-(3-methacryloxy-2-hydroxypropyl-2-isopropyl-1,3-oxazolidine and 3-(3methacryloxy-2-hydroxypropyl-2-isopropyl-1,3-oxazolidine and 3-(3 -acryloxy-2-hydroxypropyl)-2-isopropyl-1,3-oxazolidine.

Upon substituting adipic acid, azelaic acid, isophthalic acid or an acid terminated ethylene glycol adipate (ADA/EG) for the "polymeric acid mixture" of the preceding paragraph and following substantially the procedure described therein, there was thus obtained the corresponding bis-oxazolidine ester products. The following table sets forth the starting materials employed, the reaction conditions and the amount of product obtained:

TABLE I

Bis-Oxazolidines Derived From N-Glycidyl-2-Isopropyloxazolidine and Bis-Acid Condensation

| ACID | TEMP. | HOUR/SOLVENT | % ACID CONVERSION | —R¹⁰— |
|---|---|---|---|---|
| Adipic | 84°C. | 12.5/Acetonitrile | 78% | —$(CH_2)_4$— |
| Azelaic | 80°C. | 12.0/Toluene | 79% | —$(CH_2)_7$— |
| Ethylene Glycol Adipate (ADA/EG) | 80°C. | 20.0/No Solvent | 78% | $\pm(CH_2)_4-COCH_2CH_2OC\rceil_m(CH_2)_4-$ |
| Isophthalic | 80°C. | 11.5/Toluene | 80% | (phenyl) |

In a similar manner polyoxazolidines were obtained by substituting the appropriate polyacid for the "polymeric acid mixture" of the present Example and following substantially the procedure described therein.

The following Table sets forth the polyacids employed, the appropriate reaction conditions and the amount of product obtained thereby:

TABLE II

Polyoxazolidines Derived From N-Glycidyl-2-Isopropyloxazolidine and Poly-Acid Condensations

| ACIDS | TEMP. | HOURS/SOLVENT | % ACID CONVERSION |
|---|---|---|---|
| BA/MMA/MAA 75 20 5 | 85°C. | 12/No Solvent | 86% |
| BA/MMA/MAA | 85°C. | 15/No Solvent | 85% |
| BA/MMA/MAA 57 35 8 | 85°C. | 15/No Solvent | 90% |
| MAA* 17.2g. | 85°C | 7/Toluene | 70% |

The abbreviations under "ACIDS" have the following meaning:

| BA : | Butyl acrylate |
|---|---|
| MMA: | Methyl methacrylate |
| MAA: | Methacrylic acid |
| *MAA: | A copolymer of methacrylicaacid |

EXAMPLE 3

N-Glycidyl-2,2-Dihydrooxazolidine

Into a precooled three-necked flask (500 cc) equipped with a mechanical stirrer, Dean-Stark trap attached to a condenser and a thermometer attached to a Thermowatch, was charged 3-(3-chloro-2-hydroxypropyl-1,3-oxazolidine (207 g., 1.0 mole), a 36% solution of formalin (81g., 1 mole) and toluene (150cc.). The mixture was stirred for 2.5 hours whereupon gas liquid chromatography indicated that the mixture contained 80% 3-(3-chloro-2-hydroxypropyl)-2,2-dihydro-1,3-oxazolidine. The generated isobutyraldehyde was removed by distillation at 40°C/175 mm., followed by a water/toluene azeotrop at 40°C/175mm. The pressure was further reduced to 20mm. and the remaining toluene was removed at 40°C. The light yellow chlorohydrin contained 2–3% of ionic chloride and weighed 164 g. (99%). To this solution was added 150 ml. of methanol. The mixture was then cooled to 0°–5°C. and 210g. of sodium methoxide (25% methanol solution) was added dropwise over a period of three hours. After several drops had been added, the solution became cloudy with the precipitation of sodium chloride. The mixture was stirred an additional two hours and then allowed to warm to room temperature. The solution was filtered and the filtrate was concentrated on the rotary at 35°C/20mm. As the solvent was removed more sodium chloride settled out and this material was removed by filtration. The resulting N-glycidyl-2,2-dihydrooxazolidine (126 g., 98%) was obtained as a pale yellow liquid.

Molecular distillation at 95°C./0.4mm. gave a low recovery (60%) of a colorless liquid that was 95% pure N-glycidyl-2,2-dihydrooxazolidine. Infra-red also showed the absence of an hydroxyl peak and perchloric acid titration gave an equivalent weight of 133.9 (theoret. 129.2) to confirm the structure of the said product.

EXAMPLE 4

N-Glycidyl-2,2-Pentamethyleneoxazolidine

Step A: 2,2-Pentamethyleneoxazolidine

Into a one liter, three-necked flask equipped with a mechanical stirrer, dropping funnel and a Dean Stark trap attached to a condenser were placed 244 g., (4.0 moles) of ethanolamine. Cyclohexanone (68 g., 0.7 moles) was dropped in rapidly whereupon the temperature began to rise and 250 cc. of toluene was added to the solution. The remaining cylcohexanone (324 g., 3.3 moles) was added dropwise over a one hour period and the temperature rose to 60°C. The mixture was heated to reflux and 73.5 ml. of water was collected. Upon cooling, the solvent was removed in vacuo and the resulting residue was distilled at 100°C./20mm. to afford 490 g. (86.8% yield) of 2,2-pentamethyleneoxazolidine as a colorless liquid.

Analysis for $C_8H_{15}NO$; Calculated: C,68.04; H, 10.70; N, 9.91. Found: C,68.32; H,10.41; N,9.54.

Neutralization Equivalent ($HClO_4$) Calculated: 141.21; Found: 140.1.

GLC Analysis: 98+% purity

Step B: N-Glycidyl-2,2-Pentamethyleneoxazolidine

Upon treating the 2,2-pentamethyleneoxazolidine of Step A with an equivalent amount of epichlorohydrin according to the procedure described in Example 1, Step B, there is obtained 1-(1-chloro-2-hydroxypropyl)-2,2-pentamethyleneoxazolidine which, when subjected to dehydrohalogenation according to the method described in Example 1, Step C, affords N-glycidyl-2,2-pentamethyleneoxazolidine.

EXAMPLE 5

N-Glycidyl-2,2-Pentamethyleneoxazolidine

Into a three-necked flask (500cc) precooled to 5°–10°C and equipped with a mechanical stirrer, Dean-Stark trap attached to a condenser and a thermometer attached to a thermowatch, is charged 207 g. (1.0 mole) of 1-(1-chloro-2-hydroxypropyl)-2-isopropyloxazolidine, 98 g. (1 mole) of cyclohexanone and 150 cc. of toluene. The mixture is stirred for 3–4 hours and the generated iobutyraldehyde is removed by distillation at 40°C/175mm. followed by the removal of a water/toluene azeotrope at 40°C/70mm. The pressure is further reduced to about 20mm. and the remaining toluene is removed at 40°C. To the product in the flask is added 150 ml. of methanol and the resulting solution is then cooled to 0°–5°C. over a period of three hours. A 25% methanolic solution of sodium methoxide (210g.) is then added dropwise and, after the addition is completed, stirring is continued for two additional hours and the mixture is allowed to warm to room temperature. The resulting solution is filtered and the solvent removed at 35°C/20mm. to afford N-glycidyl-2,2-pentamethyleneoxazolidine.

EXAMPLE 6

3-(3-Methoxy-2-Hydroxypropyl)-2-Isopropyl-1,3-Oxazolidine

Into a 500 ml., three-neck flask equipped with a mechanical stirrer, dropping funnel and condenser with a drying tube was charged 171 g. (1 mole) of 3-glycidyl-2-isopropyloxazolidine and 250 cc. of absolute methanol. While stirring at room temperature an equivalent amount of sodium methoxide (25% solution methanol) was added over a 30 minute period. The mixture was stirred an additional two hours after addition was completed. The solvent was then removed in vacuo to afford 3-(3-methoxy-2-hydroxypropyl)-2-isopropyl-1,3-oxazolidine.

EXAMPLE 7

3-(3-Azido-2-Hydroxypropyl)-2-Isopropyl-1,3-Oxazolidine

Into a 500 ml., three-neck flask equipped with a mechanical stirrer, thermometer attached to a thermowatch, temperature controller and a condenser with a drying tube, is charged 171g. (1 mole) of 3-glycidyl-2-isopropyloxazolidine, 71.5g (1.1 mole) sodium azide and 250 cc of dioxane. The mixture is stirred and heated at 80°C for 6–8 hours and the solvent is then removed in vacuo to afford 3-(3-azido-2-hydroxypropyl)-2-isopropyl-1,3-oxazolidine.

Upon substituting the appropriate mercaptan, amine, alkali metal thiosulfate or alkali metal cyanide for the sodium azide of Example 7 and following substantially the procedure described therein there is thus obtained the corresponding 3-(3-substituted-2-hydroxypropyl)-2-isopropyl-1,3-oxazolidine. The following equation illustrates the process of Example 7 and together with Table III (infra) describes the starting materials which may be used in the said process and the products obtained thereby:

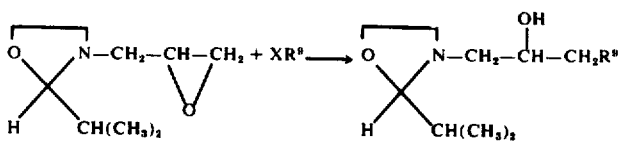

TABLE III

| EXAMPLE | XR" | —R" |
|---------|-----|-----|
| 8 | HSCH₃ | —SCH₃ |
| 9 | H₂N(CH₂)₃CH₃ | —NH(CH₂)₃CH₃ |
| 10 | Na₂S₂O₃ | —S₂O₃Na |
| 11 | HSC₂H₅ | —SC₂H₅ |
| 12 | NaCN | —CN |
| 13 | H₂NCH₃ | —NHCH₃ |

TABLE III-continued

| EXAMPLE | XR" | —R" |
|---------|-----|-----|
| 14 | NH₃ | —NH₂ |
| 15 | HS(CH₂)₃CH₃ | —S(CH₂)₃CH₃ |

What is claimed is:

1. An N-glycidyl-1,3-oxazolidine of the formula

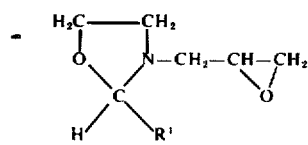

wherein R¹ is hydrogen or a hydrocarbyl radical selected from the group consisting of alkyl groups having 1 to 4 carbon atoms, and aralkyl groups selected from benzyl, phenethyl, and menaphthyl.

2. An N-glycidyl-1,3-oxazolidine of the formula

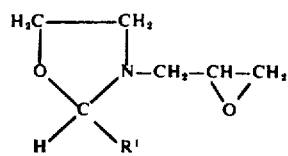

wherein R¹ is a lower alkyl group having 1 to 4 carbon atoms.

3. 3-Glycidyl-2-isopropyl-1,3-oxazolidine.
4. 3-Glycidyl-1,3-oxazolidine.

* * * * *

UNITED STATES PATENT AND TRADEMARK OFFICE
CERTIFICATE OF CORRECTION

PATENT NO. : 3,937,716
DATED : February 10, 1976
INVENTOR(S) : S.N.Lewis, J.F.Levy, N.L.Horton It is certified that error appears in the above-identified patent and that said Letters Patent are hereby corrected as shown below:

Column 2, line 13, the formula

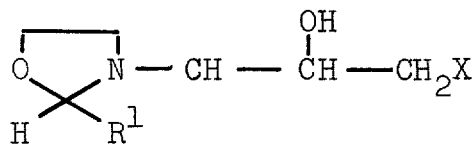

should be

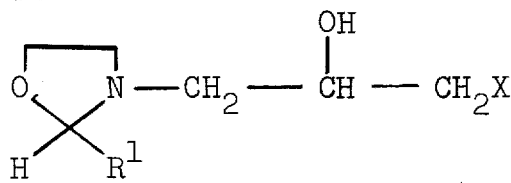

Column 9, line 6 "$(HOOC)R^9$" should be --$(HOOC)_n R^9$--.

Signed and Sealed this twenty-ninth Day of June 1976

[SEAL]

Attest:

RUTH C. MASON
Attesting Officer

C. MARSHALL DANN
Commissioner of Patents and Trademarks